United States Patent
Shimizu et al.

(10) Patent No.: US 9,681,849 B2
(45) Date of Patent: Jun. 20, 2017

(54) X-RAY DIAGNOSTIC APPARATUS AND X-RAY DIAGNOSTIC METHOD

(71) Applicant: Toshiba Medical Systems Corporation, Otawara-shi (JP)

(72) Inventors: Yoshinori Shimizu, Nasushiobara (JP); Yuichiro Watanabe, Yaita (JP); Yasuto Hayatsu, Otawara (JP); Ryoichi Nagae, Nasushiobara (JP); Yoshiaki Iijima, Tama (JP); Kunio Shiraishi, Otawara (JP)

(73) Assignee: Toshiba Medical Systems Corporation, Otawara-shi (JP)

( * ) Notice: Subject to any disclaimer, the term of this patent is extended or adjusted under 35 U.S.C. 154(b) by 0 days.

(21) Appl. No.: 14/741,880

(22) Filed: Jun. 17, 2015

(65) Prior Publication Data

US 2015/0366529 A1 Dec. 24, 2015

(30) Foreign Application Priority Data

Jun. 19, 2014 (JP) .................................. 2014-126706

(51) Int. Cl.
*A61B 6/00* (2006.01)
*A61B 6/12* (2006.01)
*A61F 2/82* (2013.01)

(52) U.S. Cl.
CPC .............. *A61B 6/5264* (2013.01); *A61B 6/12* (2013.01); *A61B 6/4014* (2013.01); *A61B 6/4266* (2013.01); *A61B 6/461* (2013.01); *A61B 6/466* (2013.01); *A61B 6/486* (2013.01); *A61B 6/487* (2013.01); *A61B 6/504* (2013.01);

(Continued)

(58) Field of Classification Search
CPC ....... G06T 7/0012; G06T 7/0016; G06T 7/20; G06T 7/2033; G06T 2207/10116; G06T 2207/20201; G06T 2207/30021; G06T 2207/30052; G06T 7/246; A61B 6/12;

(Continued)

(56) References Cited

U.S. PATENT DOCUMENTS 7,340,108 B2 3/2008 Florent et al. ................ 382/275
7,415,169 B2 8/2008 Florent et al. ................ 382/294

(Continued)

FOREIGN PATENT DOCUMENTS

JP 2010-131371 A 6/2010 ............... A61B 6/00

*Primary Examiner* — Andrew W Johns
(74) *Attorney, Agent, or Firm* — Oblon, McClelland, Maier & Neustadt, L.L.P.

(57) ABSTRACT

According to one embodiment, an X-ray diagnostic apparatus includes an input circuit, an X-ray tube and an X-ray detector, and processing circuitry. The input circuit converts an input operation into an electric signal and output the electric signal. The X-ray tube and the X-ray detector image X-ray images of an object. The processing circuitry detects positions of feature points of devices from the X-ray images; generates corrected images by motion correction of the X-ray images when an electric signal corresponding to an input operation for selecting a predetermined device has been input from the input circuit; and displays the corrected images as the moving image in real time. The motion correction is performed based on positions of a feature point of the selected device. At least a part of the selected device nearly stops when the X-ray images have been displayed, by the motion correction.

13 Claims, 4 Drawing Sheets

(52) U.S. Cl.
CPC ............... *A61B 6/464* (2013.01); *A61F 2/82* (2013.01); *A61F 2210/0004* (2013.01); *A61F 2250/0098* (2013.01)

(58) Field of Classification Search
CPC A61B 6/461; A61B 6/5264; A61F 2250/0098
See application file for complete search history.

(56) References Cited

U.S. PATENT DOCUMENTS

| | | | |
|---|---|---|---|
| 7,551,758 B2 | 6/2009 | Florent et al. | 382/128 |
| 7,620,221 B2 | 11/2009 | Florent et al. | 382/128 |
| 7,877,132 B2 | 1/2011 | Rongen et al. | 600/424 |
| 8,000,507 B2 | 8/2011 | Rongen et al. | 382/128 |
| 8,594,271 B2 | 11/2013 | Sakaguchi et al. | 378/4 |
| 2008/0051873 A1* | 2/2008 | Cottone et al. | 623/1.16 |
| 2010/0104167 A1* | 4/2010 | Sakaguchi et al. | 382/132 |

* cited by examiner

X-RAY DIAGNOSTIC APPARATUS AND X-RAY DIAGNOSTIC METHOD

CROSS REFERENCES TO RELATED APPLICATIONS

This application is based upon and claims the benefit of priority from Japanese Patent Application No. 2014-126706, filed on Jun. 19, 2014; the entire contents of which are incorporated herein by reference.

Further, the entire contents of Japanese Patent Application No. 2015-120244, filed on Jun. 15, 2015 are incorporated herein by reference.

FIELD

Embodiments described herein relate generally to an X-ray diagnostic apparatus and an X-ray diagnostic method.

BACKGROUND

Conventionally, as a display processing method for X-ray images of an object in which a stent has been inserted, a technique to recognize markers attached to the stent and perform a motion correction of the X-ray images on the basis of positions of the marker in order to allow observing the markers in a static state has been proposed. According to this technique, even when a stent inserted in an object has greatly moved due to the beat, X-ray images can be displayed as a moving image with the stent in a nearly static state. Therefore, the visibility of the stent can be improved.

An object of the present invention is to provide an X-ray diagnostic apparatus and an X-ray diagnostic method which can generate and display X-ray images useful for diagnosing an object in which a device, such as a stent, has been inserted.

DETAILED DESCRIPTION

In general, according to one embodiment, an X-ray diagnostic apparatus includes an input circuit, an X-ray tube and an X-ray detector, and processing circuitry. The input circuit is configured to convert an input operation by an operator into an electric signal and output the electric signal. The X-ray tube and the X-ray detector are configured to image frames of X-ray images of an object. The processing circuitry is configured to detect positions of each of feature points of devices, inserted in the object, from the X-ray images; generate corrected images sequentially by performing a motion correction of the X-ray images when an electric signal corresponding to an input operation for selecting a predetermined device out of the devices has been input from the input circuit; and display the corrected images as the moving image in real time by displaying the corrected images sequentially. The motion correction is performed based on positions of a feature point of the selected device. At least a part of the selected device nearly stops, by the motion correction, when the X-ray images have been displayed as a moving image.

Further, according to one embodiment, an X-ray diagnostic method including: converting an input operation of an input circuit by an operator into an electric signal and output the electric signal; imaging frames of X-ray images of an object using an X-ray tube and an X-ray detector; detecting positions of each of feature points of devices, inserted in the object, from the X-ray images; generating corrected images sequentially by performing a motion correction of the X-ray images when an electric signal corresponding to an input operation for selecting a predetermined device out of the devices has been input from the input circuit; and displaying the corrected images as the moving image in real time by displaying the corrected images sequentially. The motion correction is performed based on positions of a feature point of the selected device. At least a part of the selected device nearly stops, by the motion correction, when the X-ray images have been displayed as a moving image.

An X-ray diagnostic apparatus and an X-ray diagnostic method according to embodiments of the present invention will be described with reference to the accompanying drawings.

Figure 1:
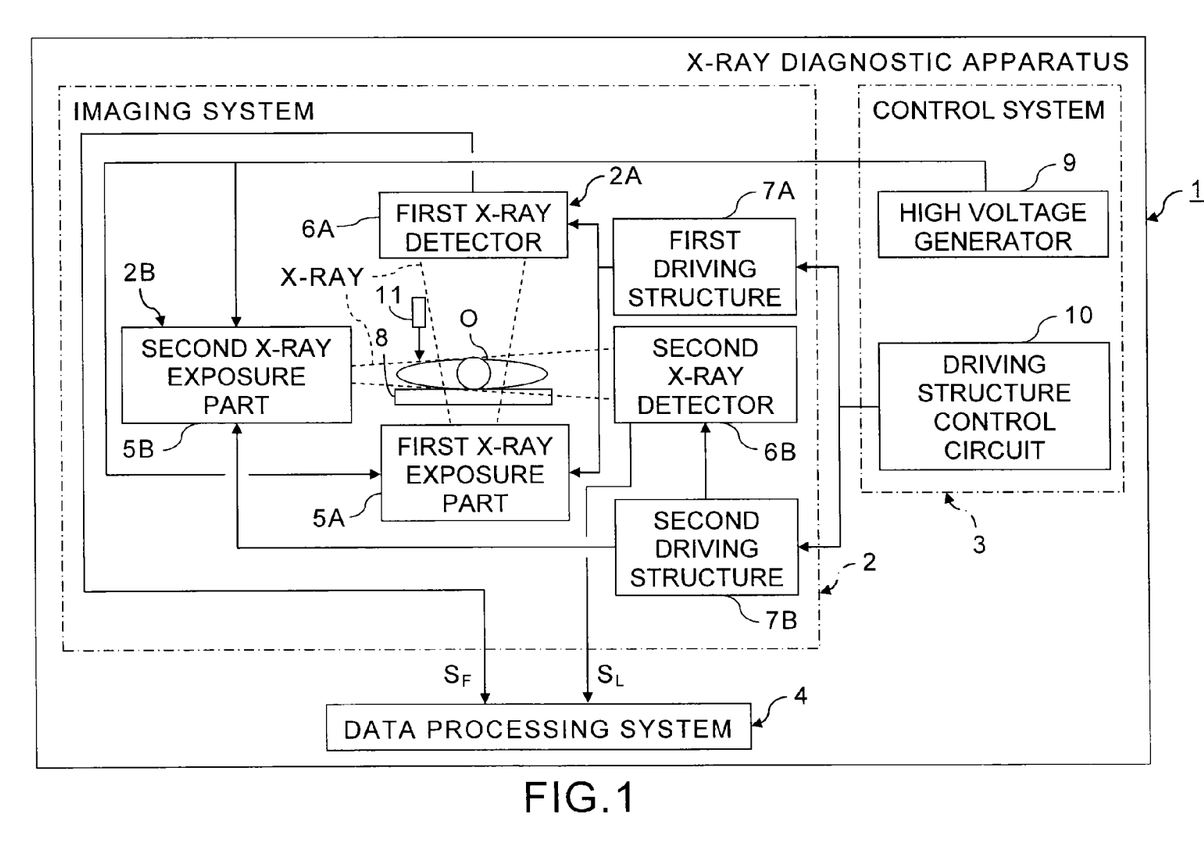
FIG. 1 is a configuration diagram of an X-ray diagnostic apparatus according to an embodiment of the present invention.
Figure 2:
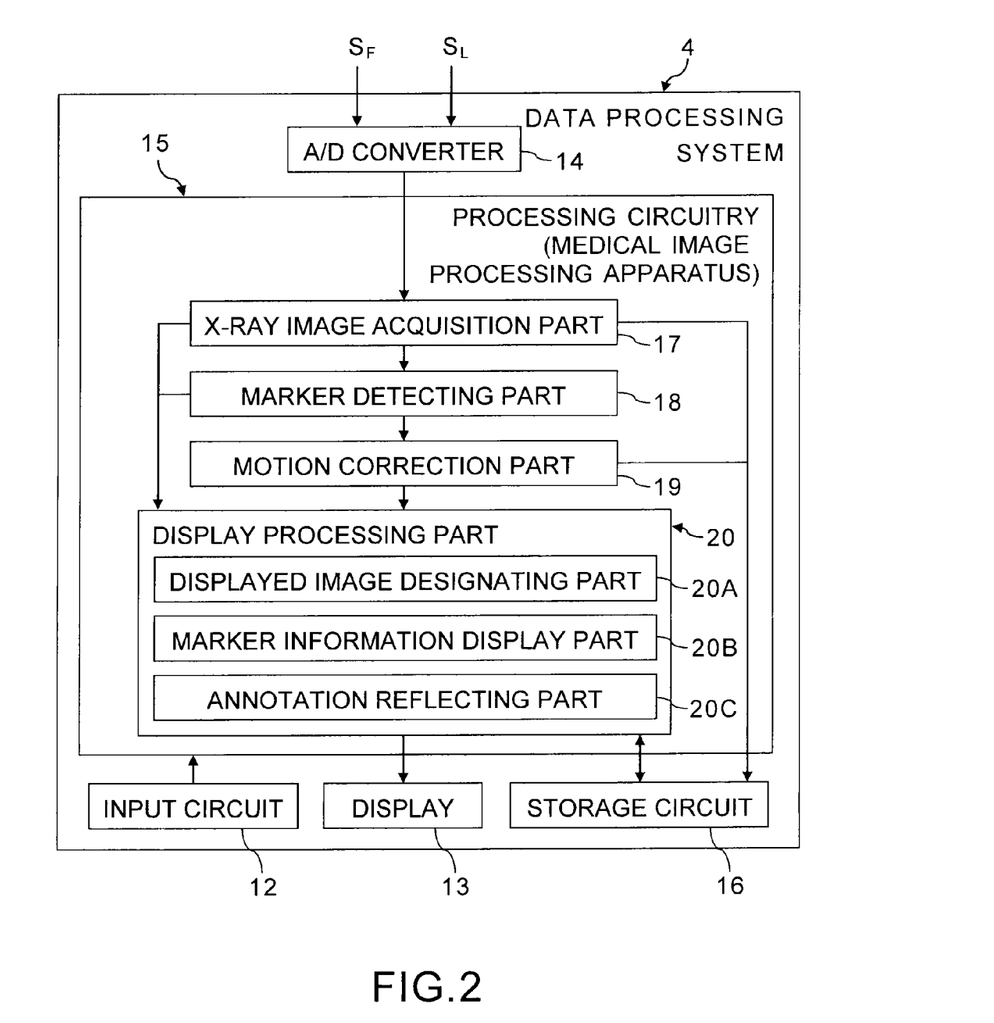
FIG. 2 is a configuration diagram of the data processing system shown in FIG. 1.

FIG. 1 is a configuration diagram of an X-ray diagnostic apparatus according to an embodiment of the present invention, and FIG. 2 is a configuration diagram of the data processing system shown in FIG. 1.

An X-ray diagnostic apparatus 1 includes an imaging system 2, a control system 3 and a data processing system 4. The imaging system 2 has the first X-ray exposure part 5A, the second X-ray exposure part 5B, the first X-ray detector 6A, the second X-ray detector 6B, the first driving structure 7A, the second driving structure 7B and a bed 8. Namely, the X-ray diagnostic apparatus 1 is a biplane type of X-ray diagnostic apparatus including the first imaging system 2A and the second imaging system 2B. The first imaging system 2A is composed of the first X-ray exposure part 5A, the first X-ray detector 6A and the first driving structure 7A. Meanwhile, the second imaging system 2B is composed of the second X-ray exposure part 5B, the second X-ray detector 6B and the second driving structure 7B.

The control system 3 has a high voltage generator 9 and a driving structure control circuit 10. Furthermore, a contrast agent injector 11 for injecting a contrast agent into an object O, set on the bed 8, is installed near the object O.

The data processing system 4 has an input circuit 12, a display 13, an A/D converter 14, processing circuitry 15 and a storage circuit 16. The processing circuitry 15 functions as an X-ray image acquisition part 17, a marker detecting part 18, a motion correction part 19 and a display processing part 20. The display processing part 20 has a displayed image designating part 20A, a marker information display part 20B and an annotation reflecting part 20C.

The first imaging system 2A is composed of the first X-ray exposure part 5A and the first X-ray detector 6A installed at the both ends of the first C-shaped arm. The first X-ray exposure part 5A and the first X-ray detector 6A are opposed to each other so that the bed 8 lies between the first X-ray exposure part 5A and the first X-ray detector 6A. Similarly, the second imaging system 2B is composed of the second X-ray exposure part 5B and the second X-ray detector 6B installed at the both ends of the second C-shaped arm. The second X-ray exposure part 5B and the second X-ray detector 6B are opposed to each other so that the bed 8 lies between the second X-ray exposure part 5B and the second X-ray detector 6B. The first driving structure 7A drives the first C-shaped arm according to control signals from the control system 3. The second driving structure 7B drives the second C-shaped arm according to control signals from the control system 3.

A typical biplane type of X-ray diagnostic apparatus for circulatory organ includes the first imaging system 2A placed on a floor and a traveling type of the second imaging system 2B which is suspended from a ceiling. The first X-ray tube included in the first X-ray exposure part 5A and the second X-ray tube included in the second X-ray exposure part 5B expose X-rays to an object O set on the bed 8 respectively. Then, the first X-ray detector 6A and the second X-ray detector 6B can detect X-ray detection data sets corresponding to two different directions.

Specifically, X-ray detection data $S_F$ corresponding to the F (Frontal) side of the object O can be acquired by the first imaging system 2A placed on the floor. Meanwhile, X-ray detection data $S_L$ corresponding to the L (Lateral) side of the object O can be acquired by the traveling type of the second imaging system 2B suspended from the ceiling.

The control system 3 controls the imaging system 2. The high voltage generator 9 of the control system 3 applies a high voltage to each of the first X-ray tube of the first X-ray exposure part 5A and the second X-ray tube of the second X-ray exposure part 5B so that the first and the second X-ray tubes expose X-rays, each having a desired energy, toward the object O. The driving structure control circuit 10 outputs control signals to the first driving structure 7A and the second driving structure 7B in order to control the first driving structure 7A and the second driving structure 7B. Specifically, a rotation angle and a position of the first X-ray exposure part 5A and the first X-ray detector 6A are controlled by control signals output from the driving structure control circuit 10 to the first driving structure 7A. Similarly, a rotation angle and a position of the second X-ray exposure part 5B and the second X-ray detector 6B are controlled by control signals output from the driving structure control circuit 10 to the second driving structure 7B.

The input circuit 12 is substantialized by a trackball, a switch button, a mouse, a keyboard, a touch panel, a touchpad or the like, for performing an operation to select a predetermined device out of devices inserted in the object O, such as a stent, and a setting of an ROI (region of interest) or the like. The input circuit 12 is connected to the processing circuitry 15 so that the input circuit 12 can convert an input operation by an operator into an electric signal to output the electric signal to the processing circuitry 15.

Next, functions of the processing circuitry 15 as a medical image processing apparatus will be described.

The processing circuitry 15 built in the X-ray diagnostic apparatus 1 can perform a variety of functions as a medical image processing apparatus, by reading programs which are stored in the storage circuit 16 and executable by a computer. That is, the X-ray image acquisition part 17, the marker detecting part 18, the motion correction part 19 and the display processing part 20 can be configured by the processing circuitry 15 consisting of a single circuit or plural circuits. For example, the processing circuitry 15 can be configured by at least one CPU (central processing unit), at least one GPU (graphics processing unit), at least one ASIC (application specific integrated circuit), and/or at least one PLD (programmable logic device), such as an SPLD (simple PLD), a CPLD (complex PLD) and an FPGA (field programmable gate array).

Note that, instead of storing programs in the storage circuit 16, the processing circuitry 15 may directly incorporate programs. In this case, the processing circuitry 15 achieves the functions by reading and executing the incorporated programs.

Furthermore, an independent medical image processing apparatus having similar functions may also be connected to the X-ray diagnostic apparatus 1 through a network. The programs to configure the medical image processing apparatus 15 can be recorded on an information recording medium to be distributed as a program product.

The X-ray image acquisition part 17 has a function to obtain digitized X-ray detection data sets $S_F$ and $S_L$ in the F side and the L side from the first X-ray detector 6A and the second X-ray detector 6B through the A/D converter 14, and generate 2D (two dimensional) or 3D (three dimensional) X-ray images in the F side and the L side respectively by performing necessary data processing of the obtained X-ray detection data sets $S_F$ and $S_L$. Therefore, when X-ray images are generated based on X-ray detection data sets $S_F$ and $S_L$ in the F side and the L side acquired in a state where a contrast agent has been injected into the object O, 2D or 3D X-ray contrast images in the F side and the L side are obtained respectively. In the fluoroscopic mode, X-ray fluoroscopic images are obtained in real time as moving images, based on time series X-ray detection data sets $S_F$ and $S_L$ in the F side and the L side.

The marker detecting part 18 has a function to detect positions of markers attached to devices, such as a stent, from each of time series frames of X-ray images of the object O in which the devices have been inserted. Detecting markers can be performed by known arbitrary image processing, such as threshold processing of pixel values.

Especially, when plural devices have been inserted in the object O, the marker detecting part 18 is configured to detect respective positions of markers attached to the devices. Specifically, the marker detecting part 18 has a function to detect positions of the first markers attached to the first device inserted in the object O and positions of the second markers attached to the second device inserted in the object O, from time series frames of X-ray images of the object O.

Examples of devices inserted in the object O include a balloon wire besides a stent, such as a bioabsorbable stent. Thus, at least one device, whose positions of markers are detection targets by the marker detecting part 18, out of devices inserted in the object O may also be a bioabsorbable stent with which markers have been attached, a balloon wire with which markers have been attached or the like.

Furthermore, the biplane X-ray diagnostic apparatus 1 as shown in FIG. 1 acquires different X-ray image data sets by the imaging system 2. Specifically, while the first time series frames of X-ray images of the object O are imaged by the first imaging system 2A of the imaging system 2, the second time series frames of X-ray images of the object O are imaged by the second imaging system 2B of the imaging system 2.

Thus, the marker detecting part 18 is configured to detect positions of the same markers attached to the same devices inserted in the object O, from each of the first time series frames of X-ray images of the object O imaged by the first imaging system 2A and the second time series frames of X-ray images of the object O imaged by the second imaging system 2B. Therefore, when the first and the second devices have been inserted in the object O, the marker detecting part 18 is configured to detect positions of the first markers attached to the first device and positions of the second markers attached to the second device, from each of the first X-ray images imaged by the first imaging system 2A and the second X-ray images imaged by the second imaging system 2B.

In case of operating devices, inserted in blood vessels, with observing X-ray fluoroscopic images which are imaged in real time by the X-ray diagnostic apparatus 1, it is sometimes desirable to display X-ray fluoroscopic images on which a device is in the static state even when the devices have greatly moved due to the beat.

Thus, the motion correction part 19 performs a motion correction, which is a correction for reducing a moving amount of at least one marker between frames of X-ray images, based on positional information on markers detected by the marker detecting part 18. More specifically, the motion correction part 19 performs coordinate conversion processing which converts respective coordinate systems of time series frames of X-ray images into coordinate systems in which at least one marker is displayed in an almost static state, i.e., coordinate systems fixed to the marker.

A typical device has plural markers. Therefore, when time series frames of X-ray images are displayed with a single coordinate system fixed to markers, it becomes possible to depict a device of which not only parallel translation but also rotational movement are almost stopped. In this case, the motion correction is coordinate conversion processing which moves coordinate systems in parallel and rotationally.

When plural devices are inserted in the object O, respective markers attached to each of the devices are detected by the marker detecting part 18. However, a moving amount is different for each device due to different in positions of the devices. Therefore, the motion correction cannot be performed to plural devices simultaneously.

Thus, when plural devices have been inserted in the object O, the motion correction part 19 performs the motion correction for every device. More specifically, while the motion correction part 19 generates the first corrected images by performing the first motion correction of X-ray images which allows positions of the first markers, attached to the first device, to be considered as static, the motion correction part 19 generates the second corrected images by performing the second motion correction of the X-ray images which allows positions of the second markers, attached to the second device, to be considered as static.

Surely, it is also possible to select a device which is a target of the motion correction, and perform the motion correction only of the selected device. In other words, the motion correction part 19 can perform the motion correction which allows positions of markers attached to a device, selected from devices according to an input operation by the input circuit 12, to be considered as static. Therefore, the motion correction part 19 functions as a UI (user interface) for selecting a device, which is a target of the motion correction, from devices according to an input operation by the input circuit 12. Note that, all devices may be targets of the motion correction to generate corrected images. In that case, a corrected image which is a target of a display may be selected from the corrected images.

Even when a single device has been inserted in the object O, the biplane X-ray diagnostic apparatus 1 images the first time series frames of X-ray images of the object O by the first imaging system 2A and the second time series frames of X-ray images of the object O by the second imaging system 2B.

Thus, the motion correction part 19 performs the first motion correction among frames of the first X-ray images, which are imaged by the first imaging system 2A, so that the first position of at least one marker detected from the first X-ray images can be considered as static. Meanwhile, the motion correction part 19 performs the second motion correction among frames of the second X-ray images, which are imaged by the second imaging system 2B, so that the second position of at least one marker detected from the second X-ray images can be considered as static. Thereby, the first corrected images and the second corrected images, in which a position of at least one marker can be considered as static, can be generated, respectively.

Therefore, when two devices, i.e., the first and the second devices have been inserted in the object O, four corrected image sets are to be generated by a motion correction for making positions, detected from the first X-ray images imaged by the first imaging system 2A, of the first markers attached to the first device nearly stop; a motion correction for making positions, detected from the first X-ray images imaged by the first imaging system 2A, of the second markers attached to the second device nearly stop; a motion correction for making positions, detected from the second X-ray images imaged by the second imaging system 2B, of the first markers attached to the first device nearly stop; and a motion correction for making positions, detected from the second X-ray images imaged by the second imaging system 2B, of the second markers attached to the second device nearly stop. When not less than three devices have been inserted in the object O, corrected images can be also generated similarly for every imaging system 2.

In case of the biplane X-ray diagnostic apparatus 1, an imaging system of which X-ray images are targets of the motion correction may be also selected from the first imaging system 2A and the second imaging system 2B. Specifically, the motion correction part 19 can perform a motion correction so that a position of at least one marker attached to a device detected from X-ray images acquired by the imaging system, selected from the first imaging system 2A and the second imaging system 2B according to an input operation by the input circuit 12, can be considered as static, similarly to a selection of device. Therefore, the motion correction part 19 also functions as a UI for selecting an imaging system, where acquired X-ray images are targets of the motion correction, from the first imaging system 2A and the second imaging system 2B according to an input operation by the input circuit 12. Note that, X-ray image sets respectively acquired by the first imaging system 2A and the second imaging system 2B may be targets of the motion correction so that corrected image sets can be generated and a displayed corrected image set can be selected from the corrected image sets.

As described above, plural markers are attached with a typical device. Thus, in case of the biplane X-ray diagnostic apparatus 1, the motion correction part 19 can be configured to generate the first corrected images and the second corrected images sequentially so that at least two points out of markers attached to a selected device become the first nearly same positions on the first corrected images and the second nearly same positions on the second corrected images, respectively, for example. Thereby, it becomes possible to display each of the first corrected images and the second corrected images in the state where parallel translation and rotation movement of the selected device have nearly stopped.

As another method, a motion correction for making a position of one point stop may also be performed based on plural markers attached to a single device. For example, a motion correction for making the midpoint of a line segment connecting two markers attached to a single device or a position of the center of gravity of markers attached to a single device stop between frames of X-ray images can be performed. In this case, corrected images where at least a part of the device, to which markers have been attached, nearly stops between frames can be generated. That is, the corrected images where one point determined based on the markers nearly stops between frames are generated as a moving image.

In this case, processing is simplified compared with a case of performing a motion correction for making at least two points of markers stop. Specifically, the motion correction can be achieved only by parallel translation of coordinate systems. Therefore, it has efficacy when a device hardly rotates or rotation movement of a device does not cause a problem. Thus, the motion correction is not only limited to a correction for making both parallel translation and rotation movement of a device negligible, but also includes a correction to an extent to reduce a moving amount of a device.

It is similar also in case of the biplane X-ray diagnostic apparatus 1. Specifically, the first corrected images and the second corrected images can be generated sequentially so that one point based on markers attached to a selected device becomes the first nearly same positions on the first corrected images and the second nearly same positions on the second corrected images. For example, the motion correction part 19 can be configured to generate the first corrected images and the second corrected images sequentially so that the midpoint of a line segment connecting two markers attached to the selected device becomes the first nearly same positions on the first corrected images and the second nearly same positions on the second corrected images.

Although corrected images may be generated as images in the same region as those of X-ray images before the motion correction, the corrected images may also be generated as images in a partial region including a device selected according to an input operation by the input circuit 12. In that case, the motion correction may be performed only for a ROI, including a target device, which has been extracted from each of the X-ray images before the motion correction. Alternatively, after performing the motion correction of the whole X-ray images before the motion correction, a ROI including a selected device may be extracted. Especially, when corrected images are generated only for a partial region including a selected device, a processing load of the processing circuitry 15 can be reduced.

The display processing part 20 has a function to perform, necessary display processing of image data generated in the medical image processing apparatus 15, and display the image data on the display 13. Especially, the display processing part 20 has a function to display corrected images, which have been generated in the motion correction part 19, in parallel on the display 13. Specifically, the display processing part 20 has a function to output, to the display 13, screen information for displaying the first corrected images, on which the first device in the static state has been depicted, and the second corrected images, on which the second device in the static state has been depicted, in parallel. Furthermore, the display processing part 20 has a function to output, to the display 13, screen information for displaying the first corrected images, which have been generated by the motion correction of the first X-ray images acquired by the first imaging system 2A, and the second corrected images, which have been generated by the motion correction of the second X-ray images acquired by the second imaging system 2B, in parallel. That is, the display processing part 20 has a function to output screen information, for displaying four corrected image sets in parallel, to the display 13.

Figure 3:
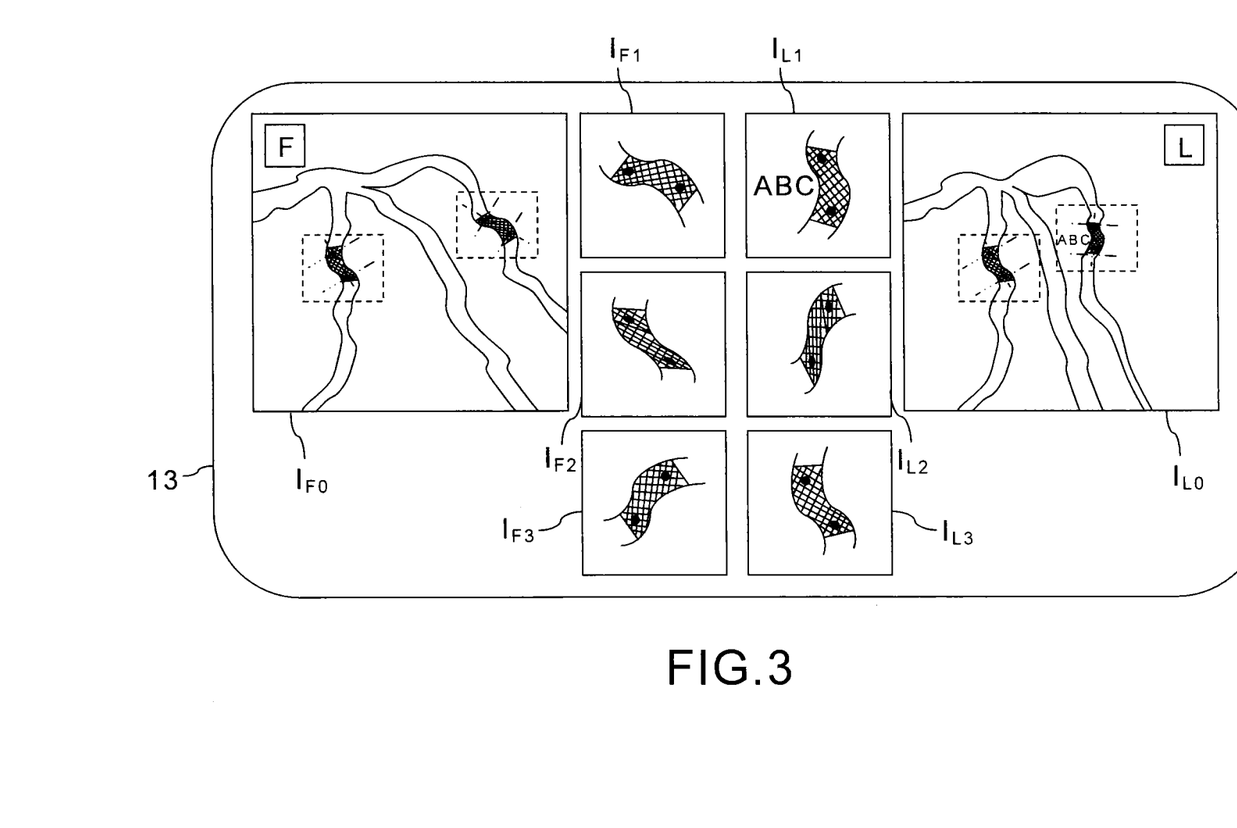
FIG. 3 shows an example of screen of the display displayed by display processing in the display processing part shown in FIG. 2.

FIG. 3 shows an example of screen of the display 13 displayed by display processing in the display processing part 20 shown in FIG. 2.

In the biplane X-ray diagnostic apparatus 1, X-ray images in the F side of the object O including devices are imaged by the first imaging system 2A, as described above. Furthermore, X-ray images in the L side of the object O including the devices are imaged by the second imaging system 2B. Therefore, respective X-ray fluoroscopic images in the F side and the L side before and after the motion correction, imaged by the first imaging system 2A and the second imaging system 2B, can be displayed in parallel as shown in FIG. 3. In an example shown in FIG. 3, an X-ray image $I_{F0}$ in the F side before the motion correction has been displayed on the left side while an X-ray image $I_{L0}$ in the L side before the motion correction has been displayed on the right side.

The displayed image designating part 20A of the display processing part 20 has a function to designate one corrected image or plural corrected images to be displayed on the display 13, based on information input from the input circuit 12. Specifically, when a user designates one target device or plural target devices from X-ray images $I_{F0}$ and $I_{L0}$ before the motion correction by operating the input circuit 12, the display processing part 20 displays corrected images, on which each designated device is depicted in a static state, on the display 13.

Specifically, the input circuit 12 converts an input operation, selecting a predetermined device out of devices inserted in the object O, by an operator into an electric signal and outputs the electric signal to the processing circuitry 15. When an electric signal corresponding to an input operation for selecting a predetermined device out of devices inserted in the object O has been input from the input circuit 12, the processing circuitry generates corrected images sequentially by performing a motion correction of X-ray images. In this case, the motion correction is performed based on positions of markers of the selected device and for nearly stopping at least a part of the selected device when the X-ray images have been displayed as a moving image. Then, the processing circuitry 15 displays the generated corrected images sequentially on the display 13 in real time as a moving image.

Especially, in case of the biplane X-ray diagnostic apparatus 1, the processing circuitry 15 detects positions of markers of a selected device, from each of frames of the first X-ray images of the object O, imaged by the first imaging system 2A including the first X-ray tube and the first X-ray detector 6A, and frames of the second X-ray images of the object O, imaged by the second imaging system 2B including the second X-ray tube and the second X-ray detector 6B. Subsequently, the processing circuitry 15 generates the first corrected images sequentially by performing the first motion correction of the first X-ray images based on the positions, which have been detected from the first X-ray images, of the markers of the selected device. By the first motion correction, at least a part of the selected device nearly stops when the first X-ray images have been displayed as the first moving image. Similarly, the processing circuitry 15 generates the second corrected images sequentially by performing the second motion correction of the second X-ray images based on the positions, which have been detected from the second X-ray images, of the markers of the selected device. By the second motion correction, at least a part of the selected device nearly stops when the second X-ray images have been displayed as the second moving image. Then, the processing circuitry 15 displays the first corrected images and the second corrected images as the first and the second moving images respectively in real time by displaying the first corrected images and the second corrected images sequentially on the display 13.

FIG. 3 shows an example of screen of the display 13 when three devices have been selected as targets to be displayed in the static state. Therefore, respective corrected images $I_{F1}$-$I_{F3}$ and $I_{L1}$-$I_{L3}$ corresponding to the F side and the L side of the first to third devices are displayed in parallel on the display 13.

Note that, although markers have been attached near the both ends of each device in the example shown in FIG. 3, an arbitrary number of markers each having an arbitrary shape may be attached to arbitrary positions of each device.

The marker information display part 20B has a function to superimpose and display information showing positions of markers, which have been detected in the marker detecting part 18, on X-ray images before the motion correction. Specifically, screen information for superimposing and displaying information showing positions of markers on X-ray images before the motion correction can be output to the display 13.

Examples of information showing positions of markers include graphics showing positions of markers respectively, a line segment connecting markers with each other, moving ranges of detected positions of markers or the like. The information showing positions of markers can be made based on coordinates of detected positions of the markers in the marker detecting part 18. For example, when positions of markers are superimposed and displayed on the X-ray images $I_{F0}$ and $I_{L0}$ before the motion correction, signs showing the positions of the markers have only to be displayed on coordinate positions of the markers, which have been detected by the marker detecting part 18. In the example shown in FIG. 3, the cross signs showing positions of markers have been displayed on the X-ray images $I_{F0}$ and $I_{L0}$ before the motion correction.

Since positions of markers vary temporally, signs showing the positions of the markers at predetermined timing, such as timing when devices which the corrected images $I_{F1}$-$I_{F3}$ and $I_{L1}$-$I_{L3}$ to be display targets correspond to have been designated, may be displayed on the X-ray images $I_{F0}$ and $I_{L0}$ before the motion correction.

Furthermore, display ranges of the corrected images $I_{F1}$-$I_{F3}$ and $I_{L1}$-$I_{L3}$ can also be superimposed and displayed on the X-ray images $I_{F0}$ and $I_{L0}$ before the motion correction. In that case, the display processing part 20 outputs, to the display 13, screen information for superimposing and displaying regions, for generating corrected images, on X-ray images before the motion correction. In the example shown in FIG. 3, respective regions for generating the corrected images $I_{F1}$-$I_{F3}$ and $I_{L1}$-$I_{L3}$ have been superimposed and displayed as rectangular frames respectively on the X-ray images $I_{F0}$ and $I_{L0}$ in the F side and the L side before the motion correction.

Therefore, a user can check rough positions of devices in an FOV (field of view) with referring to the X-ray images $I_{F0}$ and $I_{L0}$ before the motion correction and check detailed positions and/or conditions of the devices with referring to the corrected images $I_{F1}$-$I_{F3}$ and $I_{L1}$-$I_{L3}$, on which the devices are depicted in the static state.

Furthermore, a user can input annotation data, static against an arbitrary one of the corrected images $I_{F1}$-$I_{F3}$ and $I_{L1}$-$I_{L3}$, by an input operation using the input circuit 12 or another input circuit with referring to the corrected images $I_{F1}$-$I_{F3}$ and $I_{L1}$-$I_{L3}$. In this case, it is useful for diagnosis to display and attach the annotation data also on and to the X-ray images $I_{F0}$ and $I_{L0}$ before the motion correction.

Thus, the annotation reflecting part 20C has a function to reflect the annotation data, which have been input with referring to at least one of the corrected images $I_{F1}$-$I_{F3}$ and $I_{L1}$-$I_{L3}$, on the X-ray images $I_{F0}$ and $I_{L0}$ before the motion correction. Specifically, the annotation reflecting part 20C has a function to output screen information to the display 13. The output screen information superimposes and displays annotation data, input as annotation data static against a corrected image by an input operation using the input circuit 12 with referring to at least one of the corrected images, on the X-ray images before the motion correction as annotation data static against the X-ray images before the motion correction.

The processing to generate annotation data, static against X-ray images before the motion correction, based on annotation data, static against a corrected image, can be performed as inverse conversion processing of coordinate conversion processing performed as the motion correction for displaying markers in the static state.

Note that, annotation data static against X-ray images before the motion correction can be attached as incidental information with the X-ray images before the motion correction. Thereby, annotation data which have been input with referring to the corrected images $I_{F1}$-$I_{F3}$ and $I_{L1}$-$I_{L3}$ can be utilized for making a diagnostic report or the like.

Next, an operation and action of the X-ray diagnostic apparatus 1 will be described.

Figure 4:
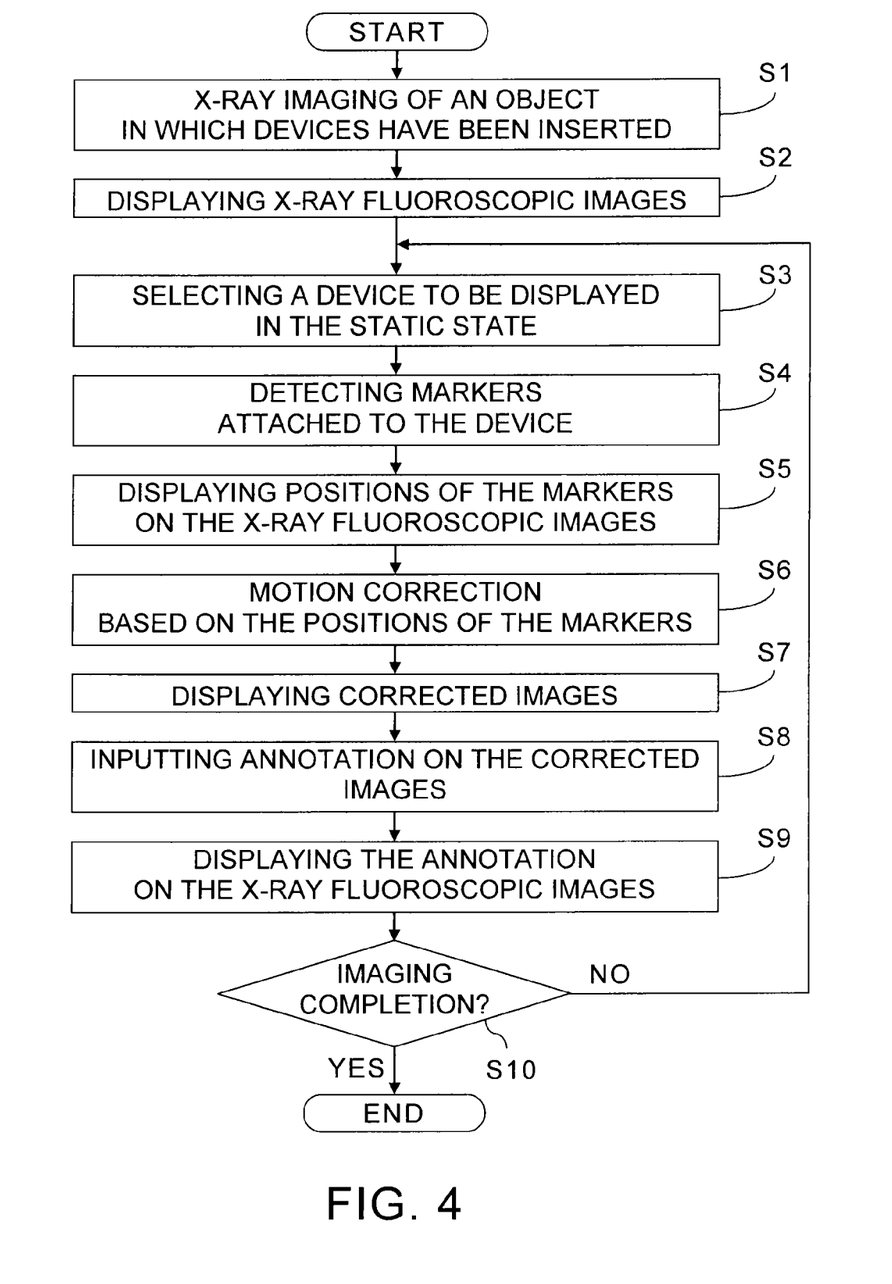
FIG. 4 is a flow chart showing an operation of the X-ray diagnostic apparatus shown in FIG. 1.

FIG. 4 is a flow chart showing an operation of the X-ray diagnostic apparatus 1 shown in FIG. 1.

Step S1 corresponds to X-ray imaging by the imaging system 2 and an X-ray image acquisition function of the processing circuitry 15. In step S1, the processing circuitry 15 achieves the X-ray image acquisition function by retrieving a predetermined program corresponding to the X-ray image acquisition function from the storage circuit 16 and executing the retrieved program.

Firstly, in step S1, a biplane X-ray fluoroscopy imaging of an object O, in which devices have been inserted, is performed.

Specifically, the object O is set on the bed 8 and a contrast agent is injected into the object O from the contrast agent injector 11 as necessary. Furthermore, devices, such as a stent, are inserted in blood vessels of the object O.

On the other hand, the first driving structure 7A and the second driving structure 7B drive according to control signals which are output from the driving structure control circuit 10. Thereby, the first X-ray exposure part 5A and the first X-ray detector 6A are positioned in a predetermined position so that the object O can be imaged from the F side. Similarly, the second X-ray exposure part 5B and the second X-ray detector 6B are positioned in a predetermined position so that the object O can be imaged from the L side.

Then, a high voltage is applied from the high voltage generator 9 to each of the first X-ray tube of the first X-ray exposure part 5A and the second X-ray tube of the second X-ray exposure part 5B. Accordingly, X-rays are exposed to the object O from the first X-ray exposure part 5A and the second X-ray exposure part 5B, respectively. The X-rays transmitting the object O from two directions are detected by the first X-ray detector 6A and the second X-ray detector 6B, respectively. The detected X-ray detection data are output to the X-ray image acquisition part 17 through the A/D converter 14. The X-ray image acquisition part 17 generates time series X-ray fluoroscopic images in the F side and the L side by necessary signal processing.

Step S2 corresponds to a display processing function of the processing circuitry 15. Specifically, in step S2, the processing circuitry 15 achieves the display processing function by retrieving a predetermined program corresponding to the display processing function from the storage circuit 16 and executing the retrieved program.

In step S2, X-ray fluoroscopic images are displayed on the display 13. Specifically, the display processing part 20 performs necessary display processing of the X-ray fluoroscopic images in the F side and the L side obtained by the X-ray image acquisition part 17, and outputs the processed X-ray fluoroscopic images to the display 13. Thereby, X-ray fluoroscopic images in the F side and the L side of the object O are displayed as live images on the display 13, as exemplified in FIG. 3.

Step S3 corresponds to a displayed image designating function of the processing circuitry 15. Specifically, in step S3, the processing circuitry 15 achieves the displayed image designating function by retrieving a predetermined program corresponding to the displayed image designating function from the storage circuit 16 and executing the retrieved program.

While a user operates a device with referring to X-ray fluoroscopic images, visual confirmation of the device may become difficult in case that the device moves by the beat. In such a case, generation of motion corrected images on which the device is depicted in the static state can be directed. When plural devices have been inserted in the object O, a device for which motion corrected images are generated is designated.

Specifically, in step S3, a device to be displayed in the static state is selected by an input operation of the input circuit 12 through an X-ray fluoroscopic image. Then, the displayed image designating part 20A specifies a device, nearest to a position selected by the input circuit 12, as a target for which motion corrected images are generated.

Step S4 corresponds to a marker detecting function of the processing circuitry 15. Specifically, in step S4, the processing circuitry 15 achieves the marker detecting function by retrieving a predetermined program corresponding to the marker detecting function from the storage circuit 16 and executing the retrieved program.

In step S4, positions of markers attached to the selected device are detected. Specifically, the marker detecting part 18 detects markers, attached to the device nearest to the position selected by the input circuit 12, from X-ray fluoroscopic image data in the F side and the L side, respectively.

Step S5 corresponds to a marker information display function of the processing circuitry 15. Specifically, in step S5, the processing circuitry 15 achieves the marker information display function by retrieving a predetermined program corresponding to the marker information display function from the storage circuit 16 and executing the retrieved program.

In step S5, the detected positions of the markers are superimposed and displayed on X-ray fluoroscopic images in the F side and the L side respectively. Specifically, the marker information display part 20B generates screen information for displaying signs, showing the positions of the markers, on coordinate positions of the markers on the respective X-ray fluoroscopic images in the F side and the L side. Then, the generated screen information is output to the display 13. Thereby, the signs showing the positions of the markers are displayed on the coordinate positions of the markers on the respective X-ray fluoroscopic images in the F side and the L side.

Step S6 corresponds to a motion correction function of the processing circuitry 15. Specifically, in step S6, the processing circuitry 15 achieves the motion correction function by retrieving a predetermined program corresponding to the motion correction function from the storage circuit 16 and executing the retrieved program.

In step S6, the motion correction part 19 performs the motion correction on the basis of the positions of the markers. Specifically, the motion correction part 19 performs coordinate conversion which converts coordinate systems of time series frames of X-ray fluoroscopic images in the F side and the L side, from a coordinate system fixed to the static system into coordinate systems fixed to at least one marker. Thereby, corrected images on which at least one marker is depicted in the static state are obtained.

Step S7 corresponds to a display processing function of the processing circuitry 15. Specifically, in step S7, the processing circuitry 15 achieves the display processing function by retrieving a predetermined program corresponding to the display processing function from the storage circuit 16 and executing the retrieved program.

In step S7, the corrected images generated by the motion correction are displayed on the display 13. Specifically, the corrected images generated by the motion correction part 19 are output to the display 13. Thereby, the corrected images on which at least one designated device is depicted in the static state are displayed on the display 13 as exemplified in FIG. 3.

On the other hand, generation regions of the corrected images can be displayed with rectangular frames or the like on the respective X-ray fluoroscopic images in the F side and the L side.

Step S8 and step S9 correspond to an annotation reflecting function of the processing circuitry 15. Specifically, in step S8 and step S9, the processing circuitry 15 achieves the annotation reflecting function by retrieving a predetermined program corresponding to the annotation reflecting function from the storage circuit 16 and executing the retrieved program.

In step S8, an annotation can be input to the corrected images by an input operation of the input circuit 12 as necessary. The input annotation is superimposed and displayed on the corrected images as incidental data of the corrected images.

Then, the annotation can also be displayed on X-ray fluoroscopic images in step S9. Specifically, the annotation reflecting part 20C converts a coordinate system of annotation data, which are input through the corrected images, from a coordinate system fixed to at least one marker into a coordinate system fixed to the static system. That is, the annotation reflecting part 20C performs inverse conversion of the motion correction on the annotation data which have become image data. Thereby, the annotation data static against X-ray fluoroscopic image data corresponding to the corrected images to which the annotation has been added are generated.

The generated annotation data are output to the display 13 with the X-ray fluoroscopic images corresponding to the corrected images to which the annotation has been added. Thereby, the annotation is superimposed and displayed on both the corrected images and the X-ray fluoroscopic images. Furthermore, the generated annotation data are stored as incidental information to the X-ray fluoroscopic images corresponding to the corrected images to which the annotation has been added. Therefore, the annotation can be displayed on the X-ray fluoroscopic images even when the X-ray fluoroscopic images are reproduced and displayed afterwards.

The above-mentioned processing from step S3 to step S9 can be repeatedly performed until the processing circuitry 15 determines the end of the imaging in step S10. Therefore, the second and subsequent devices can be additionally designated sequentially as targets to be displayed in the static state. As a result, plural devices can be designated as targets of the static display, and the corrected images on which the devices are depicted in the static state respectively can be displayed in parallel simultaneously on the display 13 as exemplified in FIG. 3. Furthermore, every time when a position of a marker is detected, the position can be additionally and sequentially highlighted on the X-ray fluoroscopic images before the motion correction.

That is, the X-ray diagnostic apparatus 1 as mentioned above is configured to display corrected images, on which a designated device is depicted in the static state, in parallel with obtained images when devices, such as a stent, have been inserted in the object O or when X-ray imaging is performed from plural directions. Furthermore, the X-ray diagnostic apparatus 1 is configured to display information useful for diagnosis, such as positions of devices or an annotation which has been input through corrected images, on obtained images.

Therefore, according to the X-ray diagnostic apparatus 1, when devices have been inserted in the object O, X-ray images on which the devices are depicted in the static state respectively can be displayed simultaneously without switching an image displayed on the display 13. In addition, in a biplane imaging, an X-ray image in the F side and an X-ray image in the L side on which a device is depicted in the static state can be displayed simultaneously. Furthermore, positions of markers detected for the motion correction can be displayed with emphasis on obtained images. Therefore, it is easy to recognize spatial positions of devices.

Moreover, information input through corrected images on which a device is depicted in the static state can also be displayed and attached on and to X-ray fluoroscopic images before the correction as supplementary information. Therefore, the input information can also be utilized for a work, such as making a report.

While certain embodiments have been described, these embodiments have been presented by way of example only, and are not intended to limit the scope of the inventions. Indeed, the novel methods and systems described herein may be embodied in a variety of other forms; furthermore, various omissions, substitutions and changes in the form of the methods and systems described herein may be made without departing from the spirit of the inventions. The accompanying claims and their equivalents are intended to cover such forms or modifications as would fall within the scope and spirit of the inventions.

For example, the above-mentioned embodiment has shown an example case where the processing circuitry 15 detects positions of markers of devices, which have been inserted in the object O, from frames of X-ray images of the object O, and generates corrected images sequentially by performing a motion correction of the X-ray images, by which at least a part of a predetermined device selected out of the devices nearly stops on the X-ray images displayed as a moving image, as a response to an electric signal, corresponding to an input operation for selecting the device, input from the input circuit 12. However, markers are one example of feature points of devices. Therefore, similar processing is available with regard to a feature point of a device other than a marker. For example, an outline of a device inserted in the object O can be extracted by edge detection processing of frames of X-ray images. Then, the X-ray images can be subjected to a motion correction for making a position of at least one feature point, such as a predetermined point on the outline of the device or the center of gravity of the device calculated based on the outline of the device, nearly stop. Thereby, corrected images can also be generated sequentially. That is, a feature point other than a marker can also be used as a feature point of a device.

Further, the above-mentioned embodiment has shown an example case where the X-ray diagnostic apparatus 1 is a biplane type. However, even in case of an apparatus, which is not a biplane type, having a single imaging system, similar display processing is available. Specifically, it is possible to generate corrected images by the motion correction of markers attached to devices, and to display the generated corrected images in parallel.

Further, the above-mentioned embodiment has shown an example case where the first X-ray exposure part 5A and the first X-ray detector 6A are opposed to each other at the both ends of the first C-shaped arm while the second X-ray exposure part 5B and the second X-ray detector 6B are opposed to each other at the both ends of the second C-shaped arm. However, the first imaging system 2A and the second imaging system 2B can be configured using arbitrary structures other than a C-shaped arm. Especially, the X-ray exposure part 5A or 5B and the X-ray detector 6A or 6B may also be arranged on independent arms, respectively, instead of arranging them at the both ends of a common arm. That is, the first imaging system 2A and the second imaging system 2B can be configured using the first arm, for positioning the X-ray exposure part 5A or 5B, and the second arm, for positioning the X-ray detector 6A or 6B, respectively. In that case, it is practical to provide driving structures, such as an expansion and contraction structure, a rotating structure, a joint structure and a link structure, for each of the first arm and the second arm.

Moreover, the first imaging system 2A and the second imaging system 2B may be attached to not only a floor and a ceiling but also wall surfaces. That is, a common arm or independent arms for holding the X-ray exposure part 5A or 5B and the X-ray detector 6A or 6B can be attached to any one of a floor, a ceiling and a wall surface.

What is claimed is:

1. An X-ray diagnostic apparatus, comprising:
an input circuit configured to convert an input operation by an operator into an electric signal and output the electric signal;
an X-ray tube and an X-ray detector configured to image frames of X-ray images of an object; and
processing circuitry configured to
detect positions of each of feature points of devices, inserted in the object, from the X-ray images,
generate corrected images sequentially by performing a motion correction of the X-ray images when an electric signal corresponding to an input operation for selecting a predetermined device out of the devices has been input from said input circuit, the motion correction being performed based on positions of a feature point of the selected device, at least a part of the selected device nearly stopping, by the motion correction, when the X-ray images have been displayed as a moving image, and
display the corrected images as the moving image in real time by displaying the corrected images sequentially,
wherein said processing circuitry is further configured to detect positions of the feature point of the selected device, from each of frames of first X-ray images of the object and frames of second X-ray images of the object, the frames of first X-ray images being imaged by a first X-ray tube and a first X-ray detector, the frames of second X-ray images being imaged by a second X-ray tube and a second X-ray detector, generate first corrected images sequentially by performing a first motion correction of the first X-ray images, the first motion correction being performed based on positions, detected from the first X-ray images, of the feature point of the selected device, at least the part of the selected device nearly stopping by the first motion correction when the first X-ray images have been displayed as a first moving image, generate second corrected images sequentially by performing a second motion correction of the second X-ray images, the second motion correction being performed based on positions, detected from the second X-ray images, of the feature point of the selected device, at least the part of the selected device nearly stopping by the second motion correction when the second X-ray images have been displayed as a second moving image, and display the first corrected images and the second corrected images as the first and second moving images respectively in real time by displaying the first corrected images and the second corrected images sequentially.

2. The X-ray diagnostic apparatus of claim 1,
wherein the feature points are markers attached to the devices, and
the devices include at least one bioabsorbable stent to which at least one marker has been attached.

3. The X-ray diagnostic apparatus of claim 1,
wherein said processing circuitry is further configured to
detect positions of a first marker attached to a first device and positions of a second marker attached to a second device, from each of the first X-ray images and the second X-ray images,
generate four corrected image sets by a motion correction for nearly stopping positions of the first marker detected from the first X-ray images, a motion correction for nearly stopping position of the second marker detected from the first X-ray images, a motion correction for nearly stopping positions of the first marker detected from the second X-ray images, and a motion correction for nearly stopping positions of the second marker detected from the second X-ray images, and
display the four corrected image sets in parallel.

4. The X-ray diagnostic apparatus of claim 1,
wherein said processing circuitry is further configured to
perform the first motion correction between the frames of the first X-ray images,
perform the second motion correction between the frames of the second X-ray images, and
display the first corrected images and the second corrected images in parallel.

5. The X-ray diagnostic apparatus of claim 1,
wherein said processing circuitry is further configured to generate the first corrected images and the second corrected images sequentially, at least two points out of markers attached to the selected device each lying nearly same first positions on the first corrected images and each lying nearly same second positions on the second corrected images.

6. The X-ray diagnostic apparatus of claim 1,
wherein said processing circuitry is further configured to generate the first corrected images and the second corrected images sequentially, one point based on markers attached to the selected device lying nearly same first positions on the first corrected images and lying nearly same second positions on the second corrected images.

7. The X-ray diagnostic apparatus of claim 1,
wherein said processing circuitry is further configured to generate the first corrected images and the second corrected images sequentially, a midpoint of a line segment connecting two markers attached to the selected device lying nearly same first positions on the first corrected images and lying nearly same second positions on the second corrected images.

8. The X-ray diagnostic apparatus of claim 1,
wherein said processing circuitry is further configured to superimpose and display annotation data, static against the X-ray images before the motion correction, on the X-ray images before the motion correction, the annotation data having been input as data static against the corrected images, by an input operation using said input circuit or another input circuit, with referring to at least one of the corrected images.

9. An X-ray diagnostic apparatus, comprising:
an input circuit configured to convert an input operation by an operator into an electric signal and output the electric signal;
an X-ray tube and an X-ray detector configured to image frames of X-ray images of an object; and
processing circuitry configured to
detect positions of each of feature points of devices, inserted in the object, from the X-ray images,
generate corrected images sequentially by performing a motion correction of the X-ray images when an electric signal corresponding to an input operation for selecting a predetermined device out of the devices has been input from said input circuit, the motion correction being performed based on positions of a feature point of the selected device, at least a part of the selected device nearly stopping, by the motion correction, when the X-ray images have been displayed as a moving image, and
display the corrected images as the moving image in real time by displaying the corrected images sequentially,
wherein said processing circuitry is further configured to superimpose and display information, showing detected positions of at least one of the feature points, on the X-ray images before the motion correction.

10. An X-ray diagnostic apparatus, comprising:
an input circuit configured to convert an input operation by an operator into an electric signal and output the electric signal;
an X-ray tube and an X-ray detector configured to image frames of X-ray images of an object; and
processing circuitry configured to
detect positions of each of feature points of devices, inserted in the object, from the X-ray images,
generate corrected images sequentially by performing a motion correction of the X-ray images when an electric signal corresponding to an input operation for selecting a predetermined device out of the devices has been input from said input circuit, the motion correction being performed based on positions of a feature point of the selected device, at least a part of the selected device nearly stopping, by the motion correction, when the X-ray images have been displayed as a moving image, and
display the corrected images as the moving image in real time by displaying the corrected images sequentially, wherein said processing circuitry is further configured to superimpose and display generation regions of corrected image sets, on the X-ray images before the motion correction.

11. An X-ray diagnostic method, comprising:
converting an input operation of an input circuit by an operator into an electric signal and output the electric signal;
imaging frames of X-ray images of an object using an X-ray tube and an X-ray detector;
detecting positions of each of feature points of devices, inserted in the object, from the X-ray images;
generating corrected images sequentially by performing a motion correction of the X-ray images when an electric signal corresponding to an input operation for selecting a predetermined device out of the devices has been input from the input circuit, the motion correction being performed based on positions of a feature point of the selected device, at least a part of the selected device nearly stopping, by the motion correction, when the X-ray images have been displayed as a moving image; and
displaying the corrected images as the moving image in real time by displaying the corrected images sequentially, wherein the method further comprises
detecting positions of the feature point of the selected device, from each of frames of first X-ray images of the object and frames of second X-ray images of the object, the frames of first X-ray images being imaged by a first X-ray tube and a first X-ray detector, the frames of second X-ray images being imaged by a second X-ray tube and a second X-ray detector,
generating first corrected images sequentially by performing a first motion correction of the first X-ray images, the first motion correction being performed based on positions, detected from the first X-ray images, of the feature point of the selected device, at least the part of the selected device nearly stopping by the first motion correction when the first X-ray images have been displayed as a first moving image,
generating second corrected images sequentially by performing a second motion correction of the second X-ray images, the second motion correction being performed based on positions, detected from the second X-ray images, of the feature point of the selected device, at least the part of the selected device nearly stopping by the second motion correction when the second X-ray images have been displayed as a second moving image, and
displaying the first corrected images and the second corrected images as the first and second moving images respectively in real time by displaying the first corrected images and the second corrected images sequentially.

12. An X-ray diagnostic method, comprising:
converting an input operation of an input circuit by an operator into an electric signal and output the electric signal;
imaging frames of X-ray images of an object using an X-ray tube and an X-ray detector;
detecting positions of each of feature points of devices, inserted in the object, from the X-ray images;
generating corrected images sequentially by performing a motion correction of the X-ray images when an electric signal corresponding to an input operation for selecting a predetermined device out of the devices has been input from the input circuit, the motion correction being performed based on positions of a feature point of the selected device, at least a part of the selected device nearly stopping, by the motion correction, when the X-ray images have been displayed as a moving image; and
displaying the corrected images as the moving image in real time by displaying the corrected images sequentially,
wherein the method further comprises superimposing and displaying information, showing detected positions of at least one of the feature points, on the X-ray images before the motion correction.

13. An X-ray diagnostic method, comprising:
converting an input operation of an input circuit by an operator into an electric signal and output the electric signal;
imaging frames of X-ray images of an object using an X-ray tube and an X-ray detector;
detecting positions of each of feature points of devices, inserted in the object, from the X-ray images;
generating corrected images sequentially by performing a motion correction of the X-ray images when an electric signal corresponding to an input operation for selecting a predetermined device out of the devices has been input from the input circuit, the motion correction being performed based on positions of a feature point of the selected device, at least a part of the selected device nearly stopping, by the motion correction, when the X-ray images have been displayed as a moving image; and
displaying the corrected images as the moving image in real time by displaying the corrected images sequentially,
wherein the method further comprises superimposing and displaying generation regions of corrected image sets on the X-ray images before the motion correction.

* * * * *